United States Patent
Maev et al.

(10) Patent No.: US 8,381,591 B2
(45) Date of Patent: Feb. 26, 2013

(54) ELECTRODE CAP FOR ULTRASONIC TESTING

(75) Inventors: Roman Gr. Maev, Windsor (CA);
Andriy M. Chertov, Windsor (CA)

(73) Assignee: Tessonics Corporation, Birmingham, MI (US)

( * ) Notice: Subject to any disclaimer, the term of this patent is extended or adjusted under 35 U.S.C. 154(b) by 296 days.

(21) Appl. No.: 12/726,453

(22) Filed: Mar. 18, 2010

(65) Prior Publication Data

US 2010/0242608 A1 Sep. 30, 2010

Related U.S. Application Data

(60) Provisional application No. 61/163,968, filed on Mar. 27, 2009.

(51) Int. Cl.
*G01N 29/04* (2006.01)
(52) U.S. Cl. .......................................................... 73/588
(58) Field of Classification Search ............. 73/588
See application file for complete search history.

(56) References Cited

U.S. PATENT DOCUMENTS

| 1,096,205 | A | 5/1914 | Taylor |
| 4,588,870 | A | 5/1986 | Nadkarni et al. |
| 6,297,467 | B1 | 10/2001 | Maev et al. |
| 7,265,313 | B2 | 9/2007 | Stevenson et al. |
| 2009/0031812 | A1 * | 2/2009 | Shibata et al. ............ 73/622 |

FOREIGN PATENT DOCUMENTS

EP 0284177 9/1988

* cited by examiner

*Primary Examiner* — Hezron E Williams
*Assistant Examiner* — Gregory J Redmann
(74) *Attorney, Agent, or Firm* — Carlson, Gaskey & Olds PC

(57) ABSTRACT

An example electrode cap includes a bored portion of an electrode cap. The bored portion establishes a bore that extends longitudinally from one end of the electrode cap and terminates at a surface having a radius relative to the longitudinal axis. A tip portion of the electrode cap extends from the surface toward another end of the electrode cap. An example method of maintaining a focal point of an ultrasonic wave includes propagating an ultrasonic wave from a transducer through a bore and a tip portion of an electrode cap and receiving a reflection of the ultrasonic wave. The method further includes determining information about a welded area using the reflection and adjusting a radius of a surface of the electrode cap to position a focal point of the ultrasonic wave within the tip portion.

16 Claims, 2 Drawing Sheets

ELECTRODE CAP FOR ULTRASONIC TESTING

REFERENCE TO RELATED APPLICATIONS

This application claims priority to U.S. Provisional Patent Application No. 61/163,968, filed Mar. 27, 2009, the contents of which are incorporated herein by reference.

BACKGROUND

This application relates generally to an electrode cap that facilitates ultrasonic testing of resistance spot welds.

As known, ultrasonic devices are sometimes used for real time quality characterization of spot welds. In reflection based designs, one transducer transmits ultrasonic waves and receives reflected ultrasonic waves. In other designs, one transducer transmits ultrasonic waves and another transducer receives the ultrasonic waves. The wave transmitted by the transducer typically propagates through an electrode cap of a welder to a weld. The received waves carry information about the welding process and reveal quality characteristics of the weld. A user interprets the ultrasonic waves to learn information about the weld.

In some designs, fluid adjacent the electrode cap carries the ultrasonic wave from the transducer to the cap. The ultrasonic wave then moves through a portion of the electrode cap before reaching the weld. As known, the electrode cap wears over time and experiences extreme temperatures during welding, which can boil and disturb the fluid. Disturbing the fluid disrupts the waves moving through the fluid and may affect the accuracy of quality information about the weld. Maintaining the focal point of the ultrasonic wave within the electrode cap is also critical to obtain accurate quality information about the weld.

SUMMARY

An example electrode cap includes a bored portion of an electrode cap. The bored portion establishes a bore that extends longitudinally from one end of the electrode cap and terminates at a surface having a radius relative to the longitudinal axis. A tip portion of the electrode cap extends from the surface toward another end of the electrode cap.

An example spot welding device includes a transducer configured to propagate an ultrasonic wave and receive a reflection of the ultrasonic wave and an electrode cap secured relative to the transducer. A tip portion of the electrode cap is configured to contact a workpiece. A bore portion of the electrode cap terminates at a radiused surface that directs a focal point of the ultrasonic wave into the tip portion.

An example method of maintaining a focal point of an ultrasonic wave includes propagating an ultrasonic wave from a transducer through a bore and a tip portion of an electrode cap and receiving a reflection of the ultrasonic wave. The method further includes determining information about a welded area using the reflection and adjusting a radius of a surface of the electrode cap to position a focal point of the ultrasonic wave within the tip portion.

These and other features of the disclosed examples can be best understood from the following specification and drawings, the following of which is a brief description:

DETAILED DESCRIPTION

Figure 1:
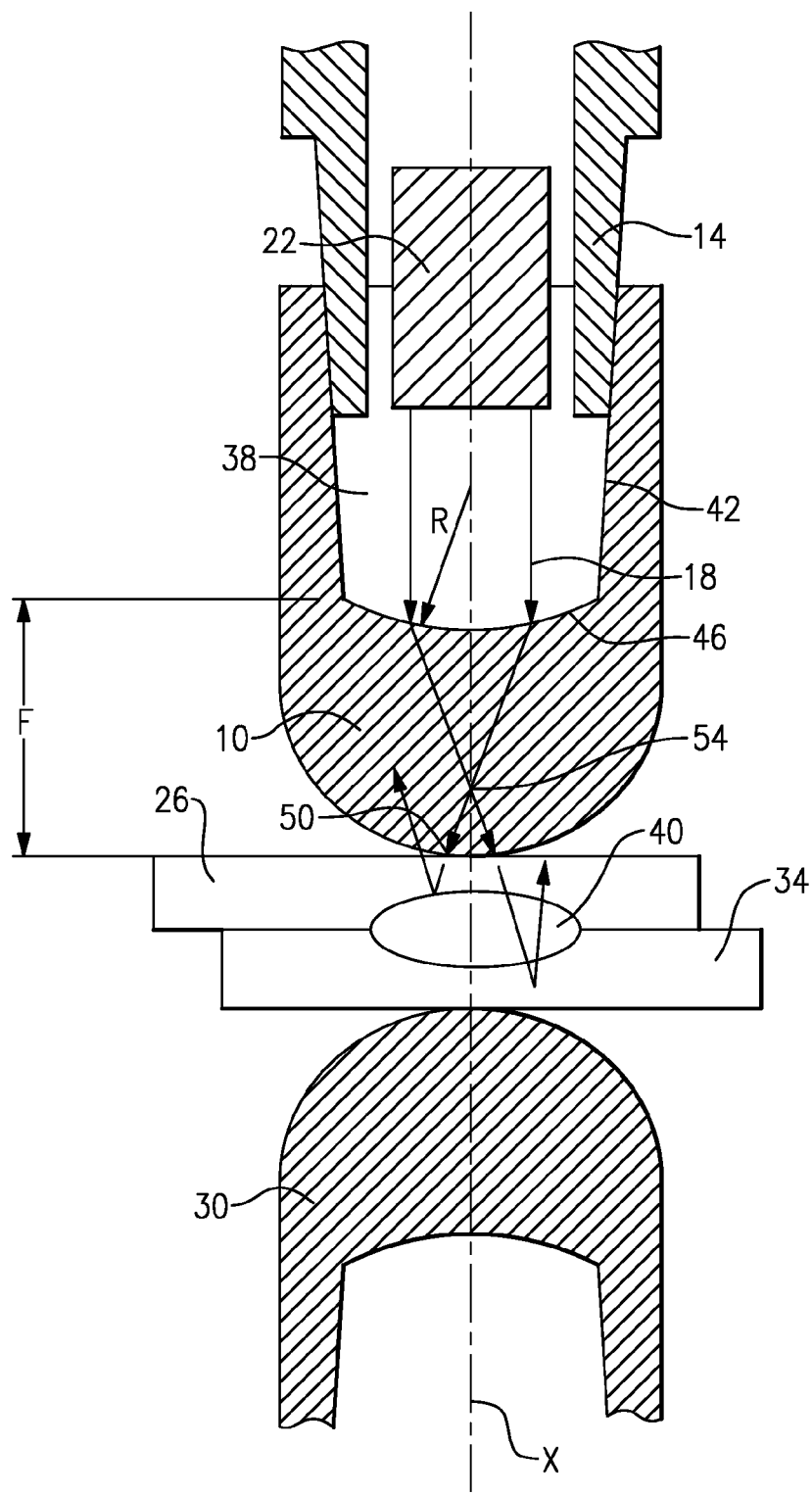
FIG. 1 shows a cross-sectional view of an example electrode cap.

Referring to FIG. 1, an example electrode cap 10 is attached to a spot welding device 14. An ultrasonic wave 18 propagates from an ultrasonic transducer 22 within the spot welding device 14 through the electrode cap 10, which is pressed against a first workpiece 26. An opposing electrode cap 30 is pressed against a second workpiece 34. The spot welding device 14 generates a spot weld 40 in a known manner that holds the first workpiece 26 relative to the second workpiece 34

In this example, the spot welding device 14 generates thermal energy, between the first workpiece 26 and second workpiece 34. The thermal energy moves from the workpieces 26 and 34 to the electrode caps 10 and 30. As known, a coolant 38 contained within a bore 42 of the electrode cap 10 carries thermal energy away from the electrode cap 10. The coolant 38 also carries the ultrasonic wave 18 from and to the ultrasonic transducer 22. The coolant 38 fills the entire bore in this example.

The bore 42 extends along a longitudinal axis X and terminates at a surface 46 having a radius R relative to the longitudinal axis X. The ultrasonic wave 18 propagates from the ultrasonic transducer 22 through the coolant 38 and then moves through the surface 46 into a portion of the electrode cap 10. The ultrasonic wave 18 propagates through the electrode cap 10 a distance F, which corresponds generally to the distance from the surface 46 to a tip face 50 of the electrode cap 10.

In this example, the ultrasonic wave 18 reflects from the first workpiece 26, the spot weld 40, and the second workpiece 34. In case of a 3-piece or 4-piece stack-up, the ultrasonic wave 18 reflects from every weld and every workpiece of the stack-up, for example. The reflected waves are received by the ultrasonic transducer 22 and used in a known manner to obtain information about the quality of the spot weld 40.

The coolant 38 and the surface 46 cause the ultrasonic wave 18 to bend or refract, for example, as the ultrasonic wave 18 propagates longitudinally. In this example, the radius R or the surface 46 is configured to position a focal point 54 of the ultrasonic wave 18 within the distance F of the electrode cap 10. Adjusting the radius R can reposition the focal point 54.

The curvature of the surface 46 can be spherical or aspherical. When spherical, the ratio of the distance F to the radius R is often between 0 and 1. The ratio is often established based on the type of coolant 38 used as coolant, the type of base material used for the electrode cap 10, and the type of welding, for example.

In one example, the electrode cap 10 is dressed, and radius R is adjusted to position the focal point 54 axially near the middle of the distance F. Positioning the focal point 54 in this area of the electrode cap 10 ensures that the focal point 54 will not extend axially beyond the tip face 50 if a portion of the electrode cap 10 wears or is dressed away during the lifetime of the electrode cap 10.

If the cap is not intended to be dressed, and the electrode cap 10 is not expected to wear more than, for example, one tenth of the distance F, the focal point 54 can be positioned axially nearer the tip face 50.

In this example, the coolant 38 is water and the electrode cap 10 is copper. When the radius R is 19.5 mm, the distance F of the electrode cap 10 typically falls within the range of 6 mm to 14.5 mm, for example. Thus, the F:R ratio often falls within the range of about 0.3 to 0.75. In one example, the distance F is 9.2 mm and the radius R is 19.5 mm, thus, the F:R ratio is about 0.47.

In another example, the F:R ratio is in the range of 0.0 to 0.6. For example, the total length of an example electrode cap having a 15.88 mm (⅝ inch) diameter is about 22.4 mm (0.88 inch), the length F of the copper base is 9.91 mm (0.39 inch), and the bottom radius of is 19.56 mm (0.77 inch). The F:R ratio of this example electrode cap would be about 0.5. The F:R ratios generally range between 0.1 to 1.0 or even 0.0 to 1.0.

Figure 2:
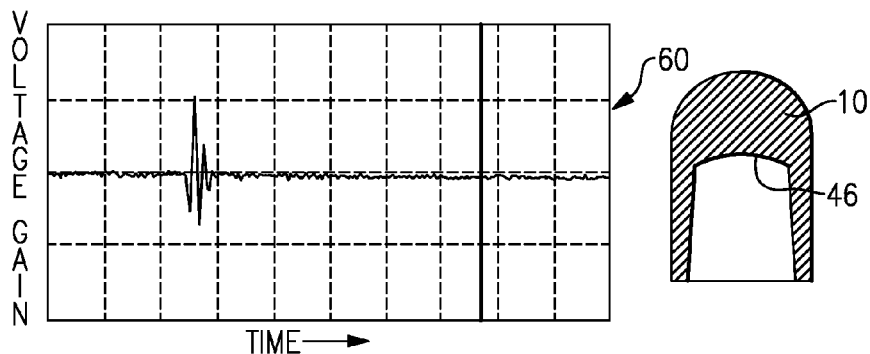
FIG. 2 shows an example graph based on an ultrasonic signal generated through the electrode cap of FIG. 1.
Figure 3:
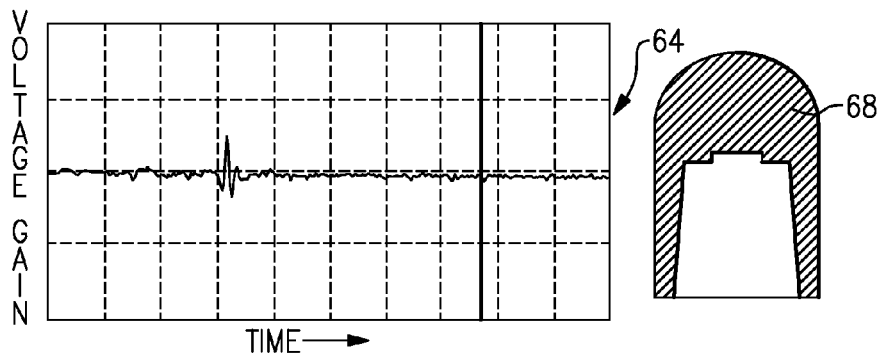
FIG. 3 shows a prior art graph based on an ultrasonic signal generated through a prior art electrode cap.

Referring to FIGS. 2 and 3 with continuing reference to FIG. 1, an example chart 60 of an ultrasonic wave 18 propagated through the electrode cap 10 is exaggerated more than the prior art chart 64. A prior art electrode cap 68, which lacks the radiused surface 46, was used when producing the prior art chart 24. The signal to noise ratio of the signal is greater in the chart 60 than the chart 64, which illustrates that the ultrasonic wave 18 propagating from the electrode cap 10 is less disturbed than an ultrasonic wave propagating from the prior art electrode cap 68. In other examples, varying the radius between 15 and 25 mm provides graphical results similar to those shown in the chart 60.

Figure 4:
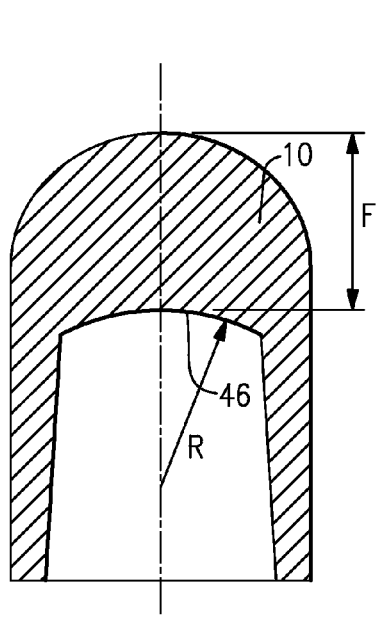
FIG. 4 shows a cross-sectional view of the FIG. 1 example electrode cap.
Figure 5:
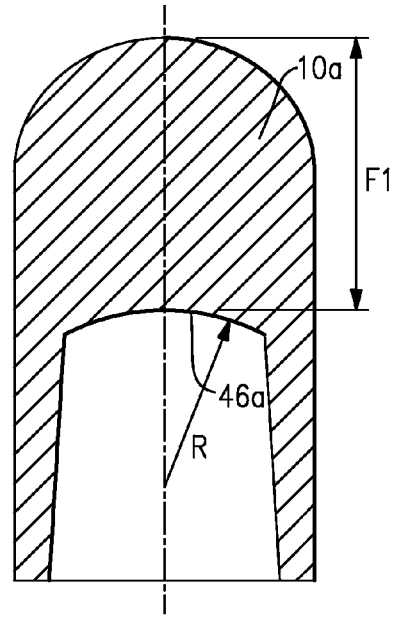
FIG. 5 shows a cross-sectional view of an example heavy duty electrode cap.

Referring to FIGS. 4 and 5 within continuing reference to FIG. 1, variations of the electrode cap 10 are possible. For example, a heavy duty electrode cap 10a having the radiused surface 46a, has a distance F1 that is about 2 mm to 4 mm longer than a distance F of the electrode cap 10. The increased distance F of the electrode cap 10 facilitates maintaining the focal point 54 within the electrode cap 10.

Increasing the distance F also increases the amount of time before thermal energy transfers from electrode cap 10 to the coolant 38. For example, when cooling water is used to convey the ultrasonic wave 28 from the ultrasonic transducer 22 to the electrode cap 10, the temperature of the water often needs to be kept as stable as possible to limit disruptions in the ultrasonic wave 28. For example, increasing the water temperature to the water's boiling point results in gas bubbles in the water stream. These bubbles become an obstacle which distort ultrasound and make quality measurements difficult. Increasing the length F1 between 3 mm and 5 mm from standard length of between 10 mm and 11 mm inhibits the water from rising to a temperature that results bubble formation.

In one example, the radius of about 19 mm is appropriate for both the electrode cap 10, which has a total length of about 22 mm, and the heavy duty electrode cap 10a, which has a total length of about 27 mm. Varying the radius between 15 mm and 25 mm in the heavy duty electrode cap 10a provide graphical results similar to those shown in the chart 64 (FIG. 3)

In some examples, the heavy duty electrode cap 10a has an F:R ratio between 0.6 and 1.0. For example, the heavy duty electrode cap 10a has a 15.88 mm (⅝ inch) diameter, a total length of 27.94 mm (1.1 inch), copper base length F of 14.99 mm (0.59 inch), and a bottom radius of 19.56 mm (0.77 inch). The F:R ratio of the heavy duty electrode cap 10a is thus about 0.76.

The preceding description is exemplary rather than limiting in nature. Variations and modifications to the disclosed examples may become apparent to those skilled in the art that do not necessarily depart from the essence of this disclosure. Thus, the scope of legal protection given to this disclosure can only be determined by studying the following claims.

The invention claimed is:

1. An electrode cap, comprising:
a bored portion of an electrode cap, the bored portion establishing a bore extending longitudinally from one end of the electrode cap and terminating at a surface that is curved relative to the longitudinal axis; and
a tip portion of the electrode cap, the tip portion extending from the surface toward another end of the electrode cap, wherein the surface is configured to position a focal point of an ultrasonic wave propagating through the electrode cap around the tip portion.

2. The electrode cap of claim 1, wherein the surface is a spherical surface.

3. The electrode cap of claim 1, wherein the tip portion has a length and the ratio of length to the radius is from 0 to 1.

4. The electrode cap of claim 1, wherein the tip portion has a length and the ratio of length to the radius is from 0.3 to 0.75.

5. The electrode cap of claim 1, wherein the radius is about 19.5 mm.

6. The electrode cap of claim 1, wherein the tip portion has a length and the ratio of length to the radius is from 0 to 0.6.

7. The electrode cap of claim 1, wherein the bore holds a coolant.

8. The electrode cap of claim 1, wherein the tip portion has a length that is from 13 mm to 16 mm.

9. The electrode cap of claim 8, wherein the radius is from 15 mm to 25 mm.

10. The electrode cap of claim 1, wherein the bore is configured to receive at least a portion of a transducer, the transducer operative to propagate an ultrasonic wave through the tip portion.

11. The electrode cap of claim 10, wherein the transducer is further configured to receive a reflected wave of the ultrasonic wave.

12. The electrode cap of claim 1, wherein the surface is an aspheric surface.

13. A spot welding device, comprising:
a transducer configured to propagate an ultrasonic wave and receive a reflection of the ultrasonic wave;
an electrode cap secured relative to the transducer;
a tip portion of the electrode cap configured to contact a workpiece; and
a bore portion of the electrode cap, the bore portion terminating at a curved surface that directs a focal point of the ultrasonic wave into the tip portion, wherein the tip portion has a length and the ratio of length to the radius is from 0 to 1.

14. The device of claim 13, wherein the curved surface is an aspheric surface.

15. An electrode cap, comprising:
a bored portion of an electrode cap, the bored portion establishing a bore extending longitudinally from one end of the electrode cap and terminating at a surface that is curved relative to the :longitudinal axis; and
a tip portion of the electrode cap, the tip portion extending from the surface toward another end of the electrode cap, wherein the longitudinal axis is a central axis, and the bore and the surface extend through a central axis.

16. The electrode cap of claim 1, wherein the longitudinal axis is a central longitudinal axis of the lower and the bored portion of the electrode cap.

* * * * *